US009360351B2

(12) United States Patent
Van Thienen et al.

(10) Patent No.: US 9,360,351 B2
(45) Date of Patent: Jun. 7, 2016

(54) BED MONITORING DEVICE (71) Applicant: Bekaert Textiles N.V., Waregem (BE)

(72) Inventors: Wim Van Thienen, Waregem (BE); Luc Vanden Bussche, Waregem (BE)

(73) Assignee: Bekaert Textiles NV, Waregem (BE)

( * ) Notice: Subject to any disclaimer, the term of this patent is extended or adjusted under 35 U.S.C. 154(b) by 0 days.

(21) Appl. No.: 14/351,949

(22) PCT Filed: Oct. 18, 2012

(86) PCT No.: PCT/EP2012/070670
§ 371 (c)(1),
(2) Date: Apr. 15, 2014

(87) PCT Pub. No.: WO2013/057200
PCT Pub. Date: Apr. 25, 2013

(65) Prior Publication Data
US 2014/0298586 A1    Oct. 9, 2014

(30) Foreign Application Priority Data
Oct. 18, 2011 (WO) ................ PCT/EP2011/068206

(51) Int. Cl.
*G01D 11/30* (2006.01)
*A61B 5/00* (2006.01)
(Continued)

(52) U.S. Cl.
CPC ............... *G01D 11/30* (2013.01); *A47C 21/00* (2013.01); *A47C 31/123* (2013.01);
(Continued)

(58) Field of Classification Search
CPC ....... G01D 11/30; G01D 5/353; G01D 5/344; A47G 9/0238; A47G 9/02; A47C 21/00; A47C 31/123; A61B 5/6892; A61B 5/0059; A61B 5/4815; A61B 5/1114; A61B 5/113; A61B 5/1116; A61B 5/1118; A61B 2562/0266
See application file for complete search history.

(56) References Cited

U.S. PATENT DOCUMENTS

| 4,822,667 | A | * | 4/1989 | Goad et al. | 442/123 |
| 5,292,013 | A | * | 3/1994 | Earl | 248/73 |
| 5,917,180 | A | * | 6/1999 | Reimer et al. | 250/227.14 |
| 6,277,770 | B1 | * | 8/2001 | Smith et al. | 442/190 |
| 6,498,652 | B1 | | 12/2002 | Varshneya et al. | |

(Continued)

FOREIGN PATENT DOCUMENTS

| EP | 1527428 A2 | 5/2005 |
| EP | 2412310 A1 | 2/2012 |
| JP | 2002219108 A | 8/2002 |
| JP | 2007144070 A | 6/2007 |
| WO | 9311553 A1 | 6/1993 |

(Continued)

OTHER PUBLICATIONS

International Search Report and Written Opinion completed Jul. 17, 2012 pertaining to International Application No. PCT/EP2011/068206.

*Primary Examiner* — Robert G Santos
*Assistant Examiner* — Myles Throop
(74) *Attorney, Agent, or Firm* — Dinsmore & Shohl LLP (57) ABSTRACT The invention relates generally to bed monitoring device for monitoring bodily activity of a person and in particular vital signs such as respiration, cardiac activity and body's physical movement, including the presence, absence, step out or even falling out of a person using a sleeping environment such as a bed; mattress; top-mattress, bedding such as mattress covers, and pillow covers; a pad; a futon and the like. Based on the monitoring of bodily activity, the bed-monitoring device further allows determining sleep comfort and sleeping position of the user. It accordingly provides a valuable R&D tool to manufacturers of sleeping articles like beds, mattresses, top-mattresses, futons and the like; but also in counselling consumers when buying sleeping articles under professional guidance. The bed monitoring device of the present invention is characterized in comprising an optical fiber fixed to or mixed into a flat body positioned within said sleeping environment. This optical fiber enables detection of bodily activity by measuring a polarization variation of light propagating through said optical fiber. Further integration of this device with other monitoring systems such as home automation and alarm systems is also possible. Further integration of this device with other monitoring systems such as home automation, bed automation and control systems, and alarm systems is also possible.

25 Claims, 7 Drawing Sheets (51) Int. Cl.
*A47C 31/12* (2006.01)
*G01D 5/353* (2006.01)
*A47C 21/00* (2006.01)
*A47G 9/02* (2006.01)
*A61B 5/11* (2006.01)
*A61B 5/113* (2006.01)
*G01D 5/34* (2006.01)

(52) U.S. Cl.
CPC ........... *A47G 9/0238* (2013.01); *A61B 5/0059* (2013.01); *A61B 5/6892* (2013.01); *G01D 5/353* (2013.01); *A61B 5/113* (2013.01); *A61B 5/1114* (2013.01); *A61B 5/1115* (2013.01); *A61B 5/1116* (2013.01); *A61B 5/1118* (2013.01); *A61B 5/4815* (2013.01); *A61B 2562/0266* (2013.01); *A61B 2562/164* (2013.01); *G01D 5/344* (2013.01)

(56) References Cited

U.S. PATENT DOCUMENTS

| | | | |
|---|---|---|---|
| 8,009,946 B2 * | 8/2011 | Xia et al. | 385/37 |
| 2006/0096776 A1 * | 5/2006 | Van De Ven | 174/111 |
| 2008/0132808 A1 * | 6/2008 | Lokhorst et al. | 600/595 |
| 2009/0070939 A1 * | 3/2009 | Hann | 5/652.1 |
| 2009/0237264 A1 * | 9/2009 | Bobey et al. | 340/815.69 |
| 2011/0185824 A1 * | 8/2011 | Mink | 73/862.624 |
| 2012/0277637 A1 * | 11/2012 | Vahdatpour et al. | 600/595 |

FOREIGN PATENT DOCUMENTS

| | | |
|---|---|---|
| WO | 2004006200 A2 | 1/2004 |
| WO | 2004006768 A1 | 1/2004 |
| WO | 2006046928 A1 | 5/2006 |
| WO | 2010110292 A1 | 9/2010 |

* cited by examiner

BED MONITORING DEVICE

The invention relates generally to bed monitoring device and mattress covers comprising said bed monitoring device, for monitoring bodily activity of a person and in particular vital signs such as respiration, cardiac activity and body's physical movement, including the presence, absence, step in/out or even falling out of a person using a sleeping environment such as a bed; mattress; top-mattress, bedding such as mattress covers, and pillow covers; a pad; a futon and the like. Based on the monitoring of bodily activity, the bed-monitoring device further allows determining sleep comfort and sleeping position of the user. It accordingly provides a valuable R&D tool to manufactures of sleeping articles like beds, mattresses, top-mattresses, futons and the like; but also in counselling consumers when buying sleeping articles under professional guidance. The bed monitoring device of the present invention is characterized in comprising an optical fibre fixed to or mixed into a flat body positioned within said sleeping environment. This optical fibre enables detection of bodily activity by measuring a polarization variation of light propagating through said optical fibre. Further integration of this device with other monitoring systems such as home automation, bed automation and control systems, and alarm systems is also possible.

BACKGROUND OF THE INVENTION

There are numerous of reasons to monitor the health and/or activity of a person occupying a bed. For example a significant cause of death in infants (birth to about 2 years) is "Crib Death" or Sudden Infant Death Syndrome (SIDS). Medical authorities generally agree that some infants simply stop breathing during sleep (apnea) or their heart rates fall dangerously low (bradycardia) and that death from these conditions can be prevented if the condition is detected and help is provided within a short time (one or two minutes) by trained personnel or parents. □ □ Apnea monitors already exist, but their cost creates an affordability problem that limits their use. Also, the existing monitors tend to be unreliable, typically having high false positive rates. Also, existing monitors are obtrusive and difficult to use because the subject must wear a belt or other device connected to the monitor. This further limits their use, and it would accordingly be desirable to have a bed-monitoring device which is both inexpensive and reliable in providing information relating to breaths, heartbeats, breathing rate, or heart rate of a monitored person.

Also in various types of care, such as medical service, geriatric care, mental health care services, etc. . . . , continuous surveillance of patients that for different reasons cannot be permitted to leave the bed single-handedly is required. For instance, it may occur that mentally deranged patients, above all in the night-time, get up from their beds and wander about in the care institution in question or even abscond from the same.

In order to address the aforementioned desire, it is known to use sensors coupled to a mattress for monitoring a bed occupant. For example PCT Publication WO 2004/006768 provides a bed occupant monitoring system comprising a plurality of optical fibres with their ends within a sheet of foam material. In order to provide a reliable output, the elasticity of the support material must be substantially the same as the elasticity of the foam material incorporating the optical fibres (see claim 10 of WO 2004/006768), posing serious limitations to the overall applicability of the bed monitoring device described therein.

PCT Publication WO 93/11553 generally describes a motion monitoring device based on a single- or multimode-optical fibre illuminated by a coherent or partially coherent light source but is silent about an optimal way of coupling such a system to a mattress.

PCT publication WO2006/046928 provides an occupant monitoring and alert system consisting of a plurality of sensor located within a mattress and characterized in consisting of an upper and lower plate of electrically conductive material and an intermediate compressible layer.

U.S. Pat. No. 6,498,652 also provide a fiber optic monitoring system for detecting vital signs of a patient, with an apparent general applicability in monitoring the health and/or activity of a person occupying a bed, but is again silent about an optimal way of coupling such a system to a mattress.

EP 2 412 310 also discloses a bed-monitoring device comprising a GI quartz-based optical fiber knitted into a cloth. As shown in FIG. 5, and explained in the description, compared to an optical fiber made from a plastic material, a GI-quartz based optical fiber provides the best measurement, with a remarkable sensitivity, hardly influenced by electrical noise or static electricity resulting from friction or the like. To live up to the required rigidity in use, and as evident from the adhesive used in the examples on file, the quartz optical fiber must be fixed and immobilized with respect to substrate support material. This limits its application in adjustable beds requiring a high degree of adaptability of the optical fiber per se.

JP 2002 219108 an optical ballistocardiograph has been described. In said device an optical fiber is anchored between rigid upper and lower plates. A stress integrator is further present to concentrate the stress that affects the optical fiber. For the same reasons as mentioned for EP 2 412 310 above, such a rigid structure has clear disadvantages when used in a sleeping environment, and accordingly fails to provide a solution to the desired hidden integration of an optical fiber in a bed occupant monitoring and alert system, in particular when applied in adjustable beds, such as for example used in the (health) care sector.

JP 2007 144070 also provides equipment for detecting pressure changes in a bed from a sleeping person, said equipment using an optical fiber bedded between the upside of the bedclothes and said person. With reference to [010] of said application, the optical fiber being fixed with adhesive tape. Compared to the present invention, the optical fiber is not well integrated into the mattress cover and fails to provide the breakpoints, that together with the further characteristics on the integration of the fiber provide an optimised integration in a sleeping environment.

It is accordingly an object of the present invention to provide a method for coupling a fiber optic monitoring system, in particular a synthetic fiber optic monitoring system to a mattress assuring a reliable method in monitoring bodily activity of a person and in particular vital signs such as respiration, cardiac activity and body's physical movement, including the presence, absence, step in/out or even falling out of a person using a sleeping environment such as a bed; mattress; top-mattress, bedding such as mattress covers, and pillow covers; a pad; a futon and the like. As will be further detailed hereinafter, the application of the optical fiber in an overlocked bag surrounded by support members comprising pressure points at discrete locations, yielded the desired reliable and hidden integration of a bed monitoring device in a sleeping environment.

Based on the monitoring of bodily activity, the device of the present invention further allows determining sleep comfort and sleeping position of the user, and accordingly provides a valuable R&D tool to manufactures of sleeping articles like beds, mattresses, futons and the like; but also in counselling consumers when buying sleeping articles under professional guidance.

These and other aspects of the present invention will become apparent to those skilled in the art after a reading of the following description of the preferred embodiment when considered with the drawings.

BRIEF DESCRIPTION OF THE DRAWINGS

FIG. 7. Details of the anchoring means used in the context of the present invention and present to prevent extraction of the optical fiber from the bed monitoring device. The anchoring means as used, consist of an anchor part (13) fixed to the base and a rode (12) connected to the optical fiber. In principle any suitable connection means, such as tape, adhesive or heat shrink, can be used to connect the rode to the optical fiber. In the present example, the rode is connected to the optical fiber by means of a heat shrink (16) through a protector cable (15) surrounding the optical fiber. Again, using this configuration, the optical fiber is not fully immobilized with respect to the base. The length of the rode still provides it with a limited freedom of movement, allowing it to adapt to changes (such as by bending of the mattress in upright position) in the sleeping environment.

The dimensions (in cm) given throughout the drawings are given as by way of example and not limiting the invention.

DETAILED DESCRIPTION OF THE INVENTION

In the following detailed description, a bed-monitoring device comprising an optical fibre fixed within an overlocked bag according to the invention will be further clarified. The intention of this description is only to further explain the general principles of the present invention, therefore nothing in this description may be interpreted as being a restriction of the field of application of the present invention or of the patent rights demanded for in the claims.

Thus in a first aspect the present invention provides a bed-monitoring system having an optical fibre (8) fixed within an overlocked bag (1) consisting of a top layer (4) and a base (5), and characterized in that the optical fibre is interlocked at the base of said overlocked bag and comprises break points, hereinafter also referred to as pressure points at discrete locations. As further explained herein below, the locations comprising said pressure points define measuring zones along said optical fiber.

As already explained hereinbefore, the optical fibre enables detection of bodily activity by measuring a polarization variation of light propagating through said optical fibre. Again with reference to the cited prior art, fixation of the optical fibre at the base of the overlocked bag is known to reduce eventual noise in the optical signal caused by independent movement of the optical fibre vis-à-vis the bed occupant. Within the context of the present invention, it has however been found that an absolute immobilization of the optical fiber with respect to substrate support material is not a requisite, and far from optimal when applied in adjustable beds. A fixation with still limited mobility of the optical fibre with respect to the substrate support material (i.e. the base of the overlocked bag), in a number of discrete zones with break points alongside the optical fibre, results in an optimal integration of such an optical measurement system in a sleeping environment, in particular when applied in adjustable beds. In other words, using support members comprising break points at regular intervals, interlocked (bound) to the base of the overlocked bag and surrounding the optical fiber, the latter is guided through the sleeping environment like a belt in a pair of trousers. The optical fiber in itself is not fixed to the substrate support material, it is only restricted in its mobility through the support members defining measuring zones alongside the optical fiber.

Where this freedom of movement of the optical fiber allows adaptability of the bed monitoring devices to changes in shape and/or orientation of the sleeping environment; e.g. when the bed is put in upward (sitting position), without affecting its performance, the absence of adhesives in positioning the fiber to the sleeping environment has further advantages in the daily application of such bed monitoring device. Assembly can be achieved using standard confection methods, e.g. all elements can be stitched and sewn together. Consequently the integration of the bed monitoring device as described herein does not change the intrinsic characteristics, such as for example moisture vapour permeability, mechanical strength, machine wash-ability, texture perception upon touch and flame resistance of the fabrics used. In addition, in case of damage to the optical fiber, it can easily be replaced by pulling a new fiber into the overlocked bag.

Figure 8:
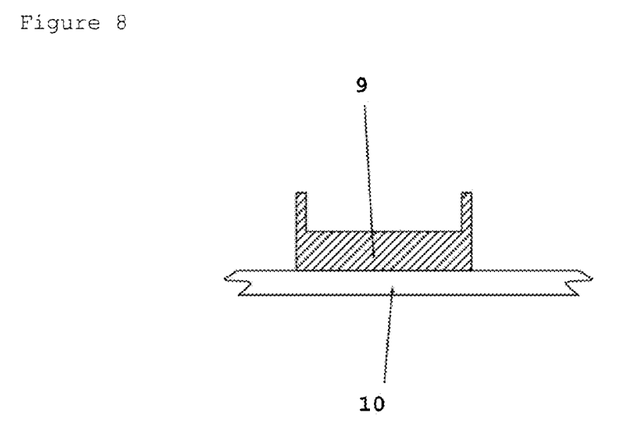
FIG. 8. Schematic cross-sectional view of the U-shaped pressure points used in particular embodiments of the present invention.

The break points as used herein generally refer to spacer or pressure points created by means of hard, rigid materials in-between the optical fiber and the top and/or base fabric of the overlocked bag. As such, pressure exerted by the user on these hard, rigid materials will create a kink or at least a deformation of the optical fiber at said points, thus disturbing the light propagating through said cable. Such pressure points can for example be realized by means of hard, rigid materials (9) such as but not limited to small blocks, slabs, strips, bands, threads or plates positioned between the optical fibre and the top and/or base fabric of the overlocked bag. In principle any material can be used to realize said pressure points provided a minimal spacer width is maintained when compressed by the user of the bed-monitoring system. In a particular embodiment of the present invention the pressure points are created by means of rigid plastic blocks, such as for example made from polyethylene described in European Patent EP1527428 fixed to the optical fibre or support members (such as slabs, strips, bands or plates) fixed to the base fabric of the overlocked bag. In one embodiment of the present invention, the pressure points are selected from the group consisting of thin, hard, rigid materials such as for example in the shape of blocks, strips, bands, threads or plates fixed to the support members at the side facing the optical fiber. In particular the pressure points are made of thin, hard, rigid U-shaped strips (49), fixed to the support member with the legs facing the optical fiber (see FIG. 8). In general the pressure points have a thickness of about 1 to 2 mm, a width of about 5 to 20 mm and a length of about 2.0 to about 6.0 cm; in particular a thickness of about 1 to 2 mm, a width of about 1.0 cm and a length from about 2.5 to about 5.5 cm.

Figure 1:
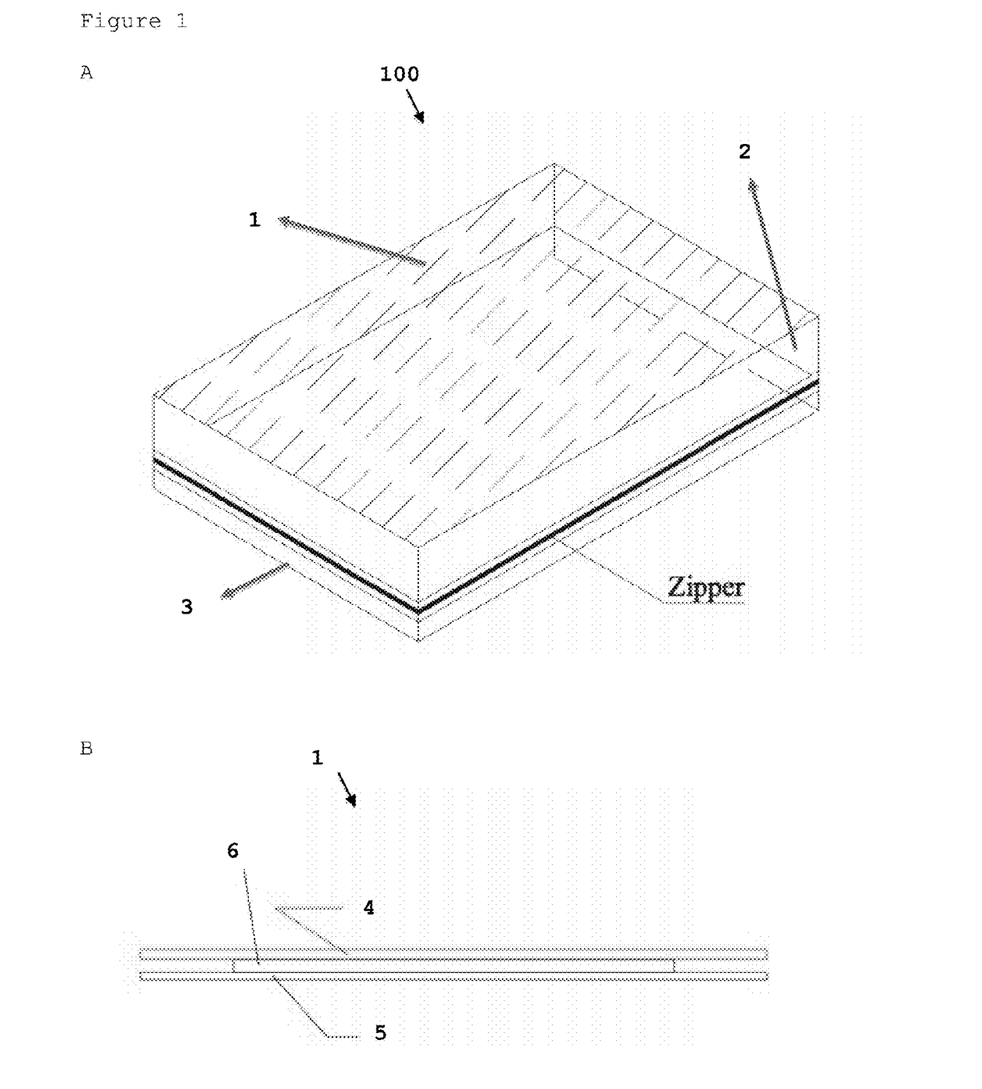
FIG. 1. Schematic drawing of a mattress cover (100) according to the present invention (A) with a cross section (B) of the overlocked bag (1), showing the top layer (4) and the base (5) forming the cavity (6) comprising the optical fibre.
Figure 2:
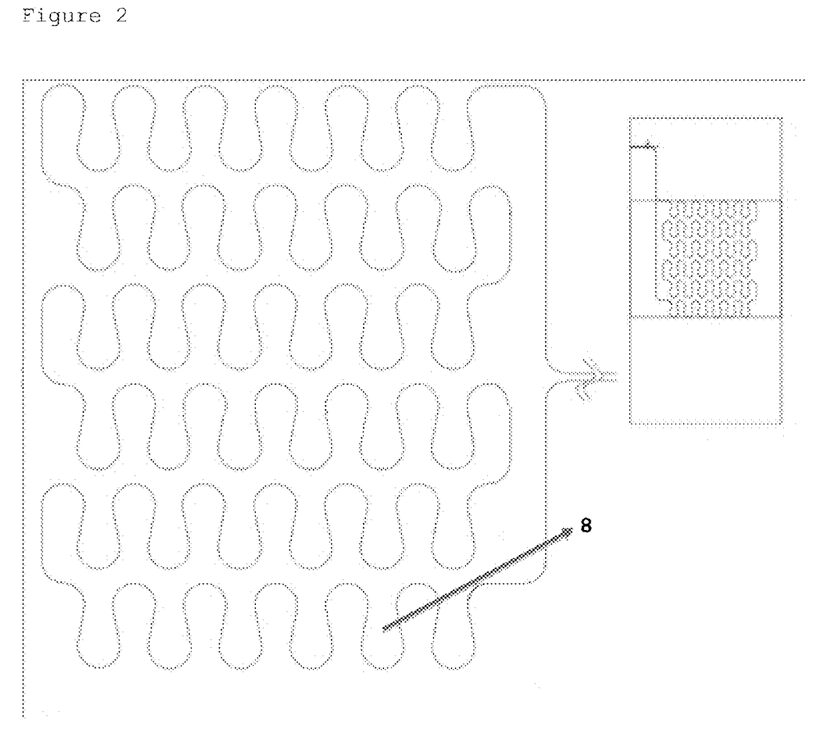
FIG. 2. Schematic drawing of the pattern and orientation/ position of an optical fibre (8) located at the chest region of a mattress cover according to the present invention.
Figure 3:
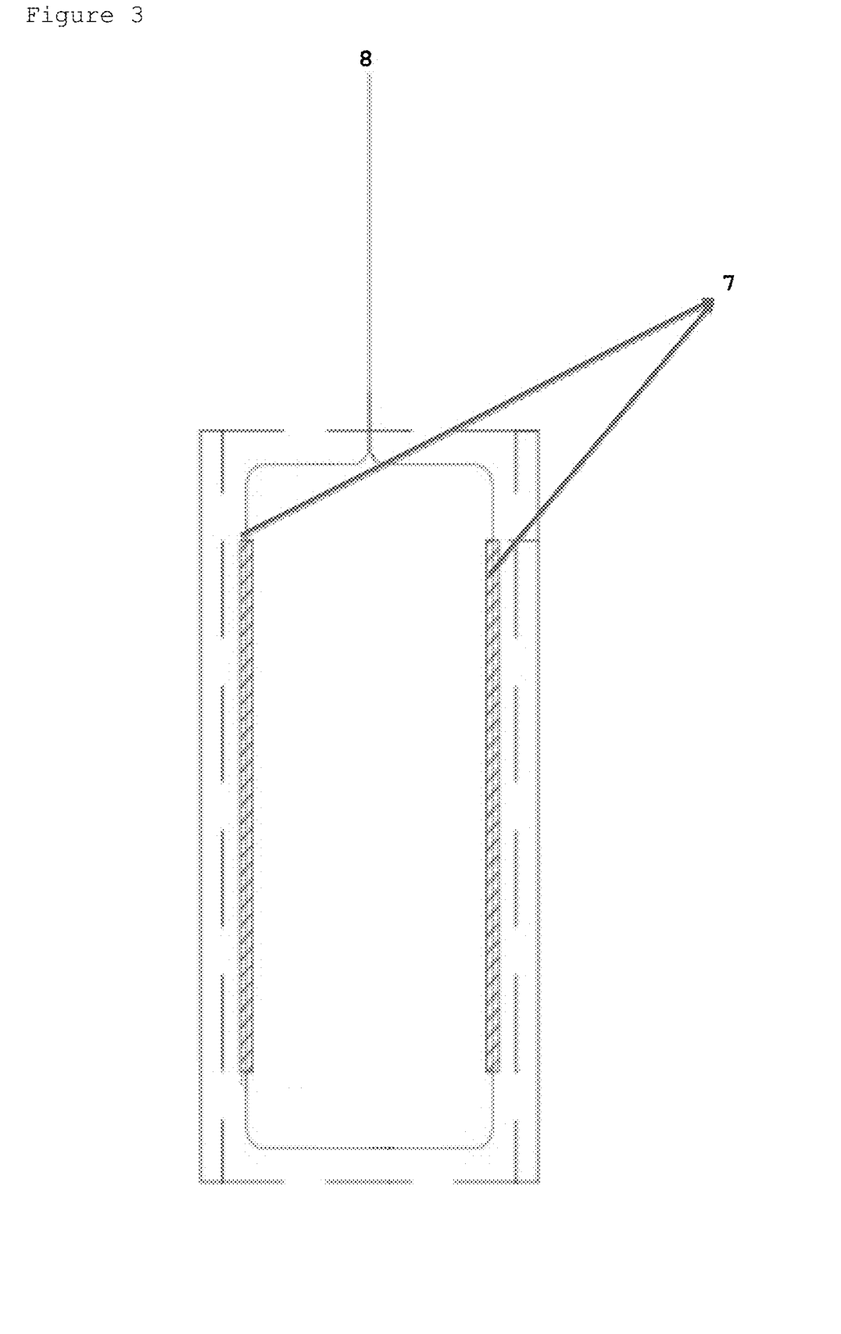
FIG. 3. Schematic drawing of a top panel (2) of a mattress cover according to the present invention wherein the optical fibres are located at the long sides (7) of the perimeter of the mattress.
Figure 4:
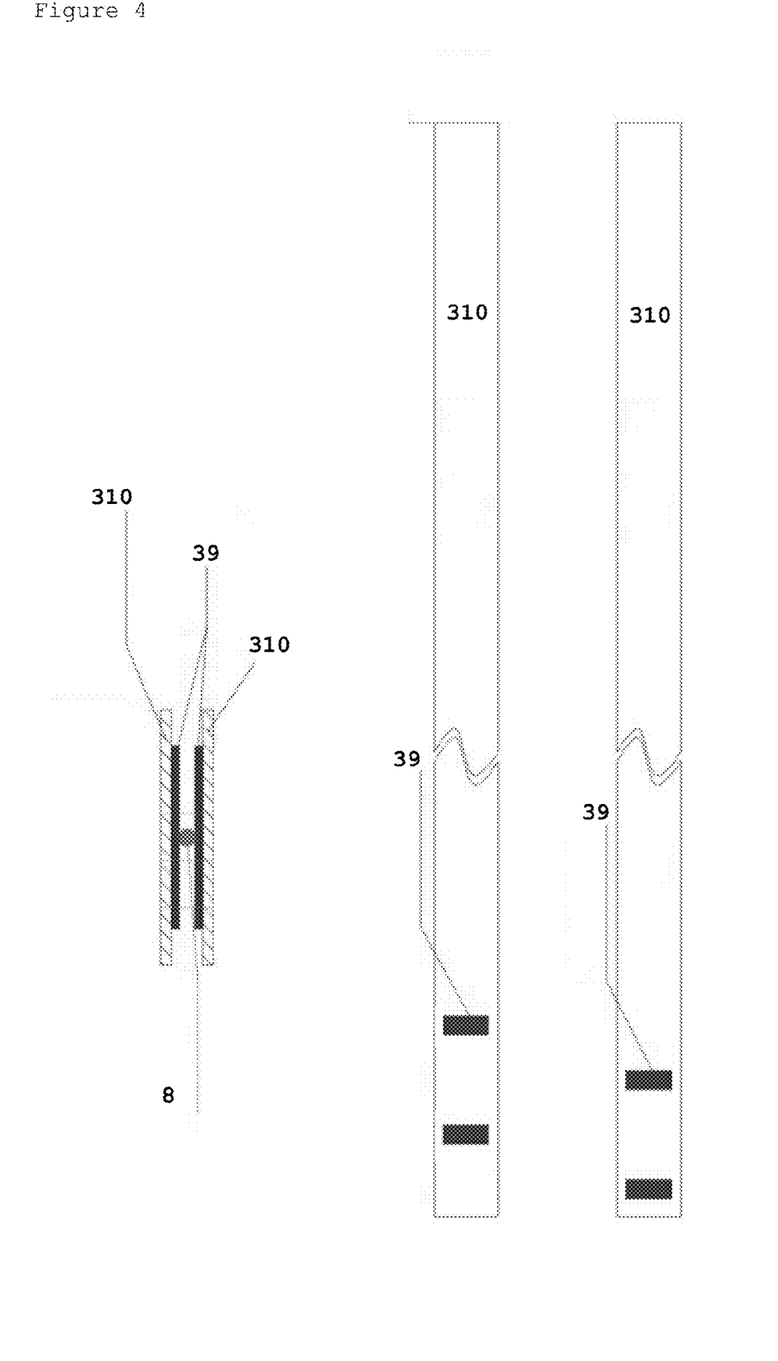
FIG. 4. Cross section and top views of members used to fix the optical fibre to the base of the overlocked bag according to one of the embodiments of the present invention. In this embodiment the break points (9) are realized by means of strips (39) fixed on tape band (310) both above and below the signal (optical) cable (8), wherein said tape bands are stitched to the base fabric (5).

The break or pressure points are present at discrete locations alongside the length of the optical fibre and in particular spaced from one another from about 5 mm to about 10 cm. As already mentioned hereinbefore, the pressure points are fixed at regular intervals to support members surrounding the optical fibre, such as shown in FIG. 4. In this embodiment the support members surrounding the optical fiber and comprising the pressure points at regular intervals, will define the measuring zones. Alongside said measuring zone the pressure point are spaced from one another from about 2.0 cm to about 10 cm; in particular spaced from one another at about every 2.5, 3.0, 3.5, 4.5, 5.0, 5.5, or 6.0 cm.

As will be apparent to the artisan skilled in the field of optical pressure sensors, the reliability and reproducibility of the signals will be dependent on a proper transfer of the bodily displacements to the optical fiber within the overlocked bag. It has been observed by the present inventors that an optimal integration and transfer is realized when discrete measuring zones are realized alongside the optical fiber using support members fixed to a substrate support material and surrounding said optical fiber, wherein said support members are further characterized in comprising pressure points at regular intervals. In an object of the present invention and as exemplified in the different embodiments shown in the accompanying figures, said substrate support material is the base of an overlock bag, in particular an overlocked bag consisting of a high weight fabric top layer (4) and an elastic back layer, in particular a light weight elastic back layer, provides optimal results.

It is thus an object of the present invention to provide a bed-monitoring device comprising an optical fiber fixed within an overlocked bag consisting of a top layer (4) and a base (5), wherein the optical fiber is interlocked at the base of said overlocked bag using one or more support members (10) defining measuring zones along said optical fiber and characterized in that said support members surround said optical fiber and comprise pressure points at regular intervals.

In its application in adjustable beds, the support material surrounding the optical fibre and restricting its mobility with respect to the substrate support, should be made of a flexible, pliant material capable of accommodating changes in shape or orientation of the bed mattress. As already mentioned herein before, using such support members, the optical fiber retains a degree of freedom in its movement with respect to the substrate support and can accordingly adjust its position in response to changes in shape or orientation of the substrate support without creating undesired kinks or even breaks in the optical fiber, that would be detrimental to the working of the optical bed-monitoring system.

Thus in a particular embodiment of the present invention, the support members comprising the pressure points are made of flexible, pliant bands, slabs or strips. More in particular made from a woven or non-woven fabric; even more in particular a pliant woven or non-woven fabric. In an even further embodiment of the present invention the support members surrounding the optical fiber and defining the measuring zones, form a sleeve or tube that slidable fits around said fiber. The sleeve are fixed (stitched) to the substrate support material (base fabric of the overlocked bag) and vary in width from about 2.0 cm to about 6.0 cm; in particular from about 3.5 cm to about 5.0 cm.

The fabrics as used herein, are meant to include any of the standard fabrics used in the manufacture of mattress covers, mattress ticking and the like, including a woven, knitted or non-woven fabric; in particular a woven or knitted fabric, such as for example but not limited to a single knit including terry velour, double knit including double jersey knit, warp knit, and woven fabrics. In addition, and in particular the top layer of the overlocked bag may consist of a spacer knitwear or spacer fabric comprises standard filler materials such as for example textured polyester, hollow polyesters fibres, nylon yarns, foam materials or the like. In other words, any woven, or knitted fabric from the collection of fabrics suitable in the manufacture of mattress covers, mattress ticking and the like can be incorporated in the overlocked bag according to the present invention. The support members are typically made from a woven or non-woven fabric of at least 100 g/m2, optionally comprising a further filler material.

In a further embodiment of the present invention the bed-monitoring device according to the present invention is further characterized in that the top layer (4) of the overlocked bag consists of a fabric with a high weight, in particular a knitted fabric with a high weight, including spacer knitwear, spacer fabric or foam materials.

In a more particular embodiment, the knitted fabric of the top layer has a weight of at least 150 g/m2; in particular of at least 250 g/m2; more in particular ranging from about 150 g/m2 to about 600 g/m2; even more in particular ranging from about 250 g/m2 to about 400 g/m2.

In an even further embodiment the bed-monitoring device according to the present invention is further characterized in that the base (5) of the overlocked bag consists of a fabric with a low weight; in particular an elastic fabric with a low weight; more in particular a knitted fabric with a low weight In a more particular embodiment, the fabric of the base has a weight of up to about 200 g/m2; in particular up to about 150 g/m2.

In principle any low-weight elastic fabric can be used as back layer (base) of the overlocked bag, including woven, non-woven and knitted fabrics, by employing elastic yarns for a part or the entire portion of the fabric. Typical examples of elastic yarns used in the manufacture of the back layer include but are not limited to elastane (lycra/spandex), rubbers, polyether-ester elastomers, elastoesters and the like.

In a particular embodiment of the present invention the fabrics used in the manufacture of the overlocked bag or either both knitted fabrics or both woven fabrics; in a more particular embodiment both fabrics are knitted fabrics with a high weight top layer as described herein and a low weight back layer as described herein.

Within the context of the present invention the 'overlocked bag' generally refers to a two-sheet material having a top layer (4) and a base (5) wherein the edges of said base material, in particular only the edges of said base material, are connected to the edges of the top material, thus creating a closed bag. In one embodiment the based layer is stitch to the top layer; alternatively the base and the top layer of the overlocked bag are removably attached to one another, such as for example by means of a zipper.

The bed-monitoring device as defined herein, is useful in monitoring bodily activity of a person using a sleeping environment such as a bed, bedding, a pad, a futon and the like. Dependent on the localization of the optical fibre within said sleeping environment, and its associated measuring zones, different bodily activities may be assessed. For example, when solely allocated in the circumference of the sleeping environment, the bed-monitoring device allows detecting of a person entering or leaving the bed. When allocated at the chest region of sleeping environment, the bed-monitoring device enables for example detection of breathing and heartbeat motion. Evidently, in an even further embodiment of the present invention, more than one optical fibre may be present within the bed-monitoring device to allow combined determination of for example bed occupancy and breathing.

Again, and as already described hereinbefore, in certain of said instances, the bed-monitoring device according to present invention comprises a spacer knitwear or spacer fabric as top layer of the overlocked bag, in a particular embodiment said spacer knitwear or spacer fabric is limited in width and length to the region wherein the optical fibre is allocated, and does not extend throughout the whole width and length of the bed-monitoring device. This constrained presence of the spacer knitwear or spacer fabric is particularly useful when the optical fibre is allocated at the circumference of the sleeping environment, more in particular at the long sides of the perimeter of the mattress. In said embodiment the spacer fabric is limited in width and length to the region wherein the optical fibre is allocated, and does not extend throughout the whole width and length of the bed-monitoring device.

Given its adaptability to the sleeping environment, the bed-monitoring device as described herein can for example be positioned on top or underneath of the mattress to detect presence, absence, step in/out or even falling out of a person using the sleeping environment.

In an exemplary embodiment the bed monitoring device comprising the optical fiber consists of an overlocked bag having a top layer and a base, wherein the optical fiber is interlocked at the base of said overlocked bag using one or more support members (10) defining measuring zones along said optical fiber and characterized in that said support members surround said optical fiber and comprise pressure points at regular intervals, and further characterized in that the top layer consists of a knitted fabric with a high weight (in particular at least 150 g/m2, preferably a multi-layered fabric) and in that the base consists of a low weight knitted fabric (in particular with a weight up to about 200 g/m2).

In other words in an embodiment of the present invention, the bed monitoring devices consists of a multi-layered overlocked bag comprising the optical fiber at its base and characterized in that the optical fiber is surrounded by support members comprising pressure points at regular intervals, thus defining measuring zones alongside said optical fiber, wherein said support members are bound to the base material. Dependent on the localization of the optical fibre within said multi-layered overlocked bag and its position within the sleeping environment different bodily activities may be assessed. In one embodiment the multi-layered overlocked bag comprises one optical fibre wherein said fibre is located within any one of the chest region, shoulder region, lower back region, hip region, upper leg region, circumference of the sleeping environment (e.g. mattress) or combinations thereof.

In another embodiment of the present invention the bed-monitoring device as described herein is part of a mattress cover. In an even further embodiment, the overlocked bag comprising the optical fibre constitutes the top panel (2) and/or the bottom panel (3) of said mattress cover and may be removably attached (for example by means of a zipper) to rest of said mattress cover. In said embodiment the fabric characteristics of the mattress cover may further influence the transfer of the bodily displacements to the optical fiber, and accordingly have an impact on the reproducibility and reliability of the measurements.

It has been observed by the present inventors, that in said embodiment the best results are obtained when the panel comprising the optical fiber is composed of a multi-layered fabric comprising a high weight filler of at least 150 g/m2 as top layer and a low weight back layer as base.

In one embodiment of the mattress cover the top panel (2) consists of the overlocked bag as described herein and a bottom panel (3) wherein; —said overlocked bag is composed of a multi-layered fabric comprising a high weight filler of at least 150 g/m2 as top layer and a low weight back layer; and wherein said bottom panel is composed of a multi-layered fabric comprising a high weight filler of at least 150 g/m2.

In another embodiment of the mattress cover the bottom panel (3) consists of the overlocked bag as described herein and a top panel (2) wherein; —said overlocked bag is composed of a multi-layered fabric comprising a high weight filler of at least 150 g/m2 as top layer and a low weight back layer; and wherein said top panel is composed of a multi-layered fabric comprising a high weight filler of at least 150 g/m2.

Thus in an even further embodiment the present invention provides a mattress cover consists of a top panel and a bottom panel wherein both the top panel (2) and the bottom panel (3) consist of the overlocked bag as described herein. In particular a mattress cover wherein the top panel or the bottom panel consists of an overlocked bag comprising an optical fibre and composed of a multi-layered fabric comprising a high weight filler of at least 150 g/m2 as top layer and a low weight back layer; and wherein said other panel is composed of a multi-layered fabric comprising a high weight filler of at least 150 g/m2.

In one embodiment the optical fibre within said bed monitoring device or mattress cover comprising said bed monitoring device, is located within the chest region of mattress. In another embodiment the optical fibre is located within the hip region of mattress, in a further embodiment the optical fibre is located within the shoulder region, in another embodiment the optical fiber is located within the lower back region, in another embodiment the optical fiber is located within the upper leg region, and in an even further embodiment the optical fibre is located in the circumference of the mattress and in particular at the long sides of the perimeter of the mattress.

Evidently in an even further embodiment, the mattress cover or overlocked bag may comprise one or more optical fibres wherein said fibres are located within the chest region, shoulder region, lower back region, hip region, upper leg region, circumference of the sleeping environment (e.g. mattress) or combinations thereof. In one embodiment the mattress cover or overlocked bag comprises one optical fibre wherein said fibre is located within any one of the chest region, shoulder region, lower back region, hip region, upper leg region, circumference of the sleeping environment (e.g. mattress) or combinations thereof.

In a particular embodiment of the bed monitoring device or of the mattress cover comprising said bed monitoring device, the optical fiber is located within the lower back, hip and upper leg region of the mattress or sleeping environment. As further shown in the accompanying figures, when allocated in the circumference of the sleeping environment (See FIG. 5) this configuration is particularly useful in determining a person entering or leaving the bed, and is accordingly useful in medical service, geriatric care, mental health care services, etc. . . . , where continuous surveillance of patients that for different reasons cannot be permitted to leave the bed is required. The system alarms the nurse/care staff from the moment the patient wants to leave his bed. Thus before a possible fall so that accidents can be avoided.

In said embodiments, wherein the measuring zones of the optical fibre are located at the circumference of the mattress or sleeping environment, the break points alongside the length of the optical fibre are realized by means of thin, hard, rigid materials (9) fixed to support members (10) at either side of, and thus surrounding the optical fibre, interlocked at the base fabric of the overlocked bag, and spaced from one another from about 2 cm to about 10 cm, in particular spaced from one another at about every 2.5, 3.0, 3.5, 4.5, 5.0, 5.5, 6.0 cm.

In said embodiments, wherein the measuring zones of the optical fibre are located within the chest region, shoulder region, lower back region, hip region, upper leg region of the mattress or sleeping environment, the break points alongside the length of the optical fibre are realized by means of thin, hard, rigid materials (9) fixed to support members (10) at either side of the optical fibre, interlocked at the base fabric of the overlocked bag, and spaced from one another from about 5 mm to about 1 cm, in particular spaced from one another at about every 2, 3, 4, 5, 6, 7, 8 or 9 cm.

In said embodiments wherein the optical fibre is located within the chest region, shoulder region, lower back region, hip region, upper leg region, the measuring zones of the optical fibre are arranged in a plurality of stripes of wavy lines across the width of the mattress cover. In particular the measuring zones of the optical fibre are arranged in at least 3, in particular up to 6 stripes, more in particular up to 10 stripes of wavy lines across the width of the mattress cover. In said embodiments the fibre is interlocked to the base of the overlocked bag, by means of support members (10) surrounding the optical fiber and comprising pressure points at regular intervals, in particular spaced from one another at about every 2, 3, 4, 5, 6, 7, 8 or 9 cm.

As already mentioned hereinbefore, dependent on the localization of the optical fibre within said sleeping environment different bodily activities may be assessed. For example, when solely allocated in the circumference of the sleeping environment, the bed-monitoring device allows detecting of a person entering or leaving the bed. When allocated at shoulder, lower back, chest, hip region, upper leg region, or combinations thereof, the bed-monitoring device enables for example detection of breathing, heartbeat motion, presence or absence of a person using the sleeping environment.

Accordingly, the present invention further provides the use of the bed-monitoring device as described herein for one or more of the following applications; detecting of a person entering or leaving the bed, breathing, heartbeat motion, presence or absence of a person using the sleeping environment. In detecting the presence or absence of a person using the sleeping environment the bed-monitoring device is either positioned on top or underneath of the mattress, futon or the like; in particular underneath of the mattress, futon or the like.

Thus in one embodiment the present invention provides a mattress cover for detecting of a person entering or leaving the bed; said mattress cover (100) comprising a top panel (2) and a bottom panel (3), wherein the top panel consists of an overlocked bag as described herein, and characterized in that the optical fibre is allocated at the circumference of the sleeping environment, more in particular with the measuring zones at the long sides of the perimeter of a mattress; even more in particular with the measuring zones below the hip zone at the long sides of the perimeter of the mattress.

Figure 5:
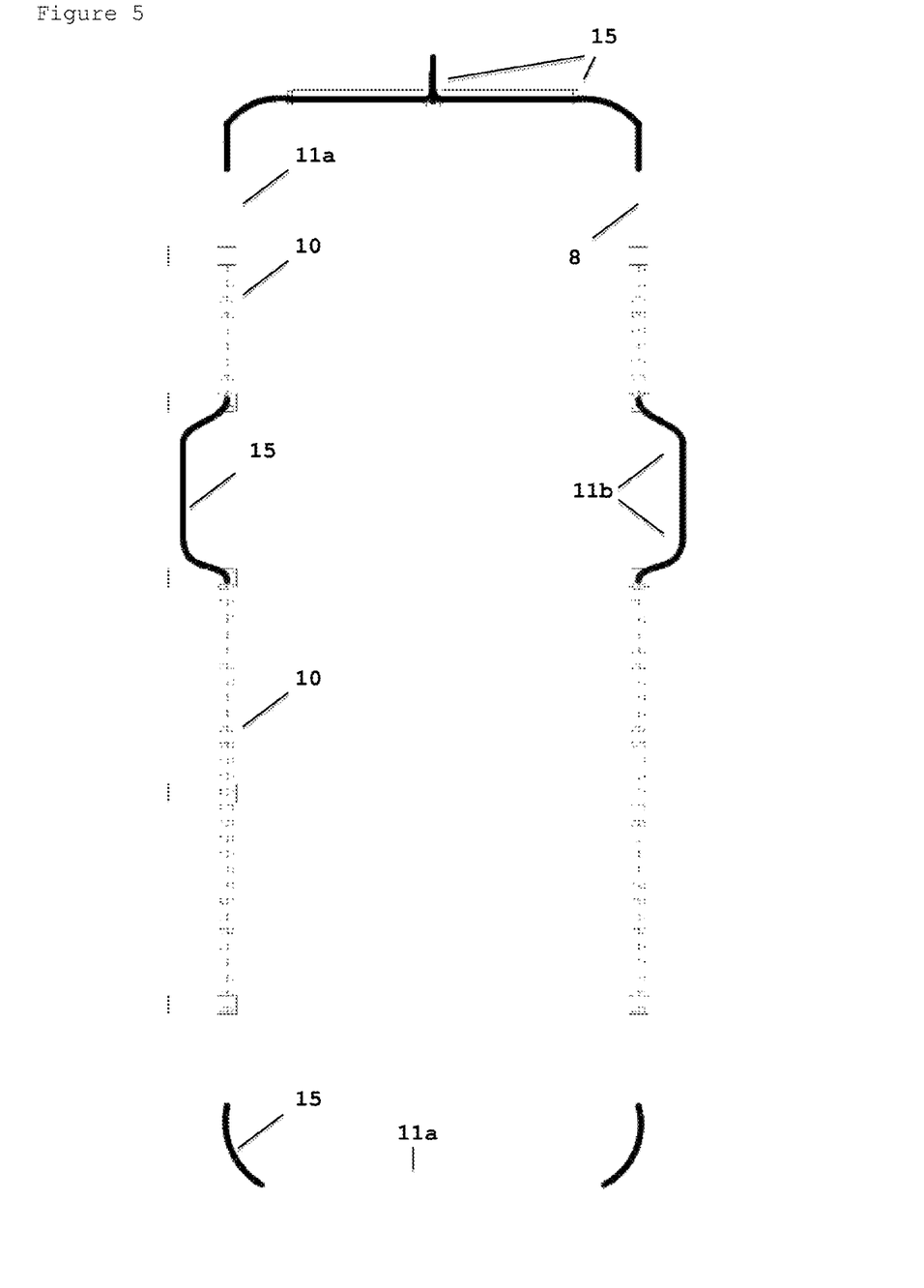
FIG. 5. Sewing design for the base of an overlock bag of the present invention having the optical fibre in its circumference. The measuring zones, consisting of the support members (10) comprising the pressure points (9), are present below the hip region. The optical fiber is further retained in the circumference of the base using long sleeve like guiding means (11*a*) in the area above the hip zone and by means of one ore more short ring-like sleeves (11*b*) in the hip region. In advert removal of the optical fiber is prevented by means of anchoring means (13) in the guiding sleeve at the top of the base.

With reference to FIG. 5, as an exemplary embodiment of the integration of the optical fiber in a bed-monitoring device according to the invention, further to the measuring zones that are allocated below the hip zone and at the long sides of the perimeter of the mattress, further guiding means (11) for the optical fiber may be present in the bed-monitoring device(s) of the present invention. In the present example they guide the optical fiber throughout the circumference of the sleeping environment, in particular in the circumference of the mattress.

Thus in an embodiment of the present invention, the bed monitoring device(s) and mattress covers as described herein may further comprise guiding means (11) for the optical fiber. Again and similar to the support members defining the measuring zones, these guiding means will not result in an absolute immobilization of the optical fiber but still allow a limited mobility of the optical fibre with respect to the substrate support material. In other words, these guiding means will consist of sleeves, tubes, rings or combinations thereof fixed to the substrate support material, and capable of slidably accommodating the optical fiber. Typically these guiding means are made from the same materials as the support members comprising the pressure points, i.e. they are made of a flexible, pliant material capable of accommodating changes in shape or orientation of the bed mattress.

Thus in a particular embodiment of the present invention, the guiding means are made of bands, slabs or strips. More in particular made from a woven or non-woven fabric; even more in particular a pliant woven or non-woven fabric. In an even further embodiment of the present invention the guiding means (11) form a sleeve or tube that slidable fits around said fiber. The sleeve are fixed (stitched (16) to the substrate support material (base fabric of the overlocked bag) and vary in width from about 2.0 cm to about 6.0 cm; in particular from about 3.5 cm to about 5.0 cm. Where the support members comprising the pressure points define measuring zones along the optical fiber, the guiding means, given the absence of the pressure points, define 'non'-measuring zones along the optical fibre. Combining such measuring and non-measuring zones along the optical fiber and throughout the sleeping environment allows tailoring the sensitivity of the bed monitoring device(s) to the requisite needs.

In the embodiment shown in FIG. 5, the absence of measuring zones in the head, shoulder and hip area greatly reduced false signals in monitoring a person entering or leaving the bed. For example the free loop of the optical fiber between the guiding means in the head to shoulder region and the measuring zone below the hip region, gives the optical fiber sufficient freedom of movement to accommodate bending of the bed in upward (sitting) position without disturbing the measuring. To protect these free loops of optical fiber from getting damaged, they may be put into a protector cable (15).

Figure 7:
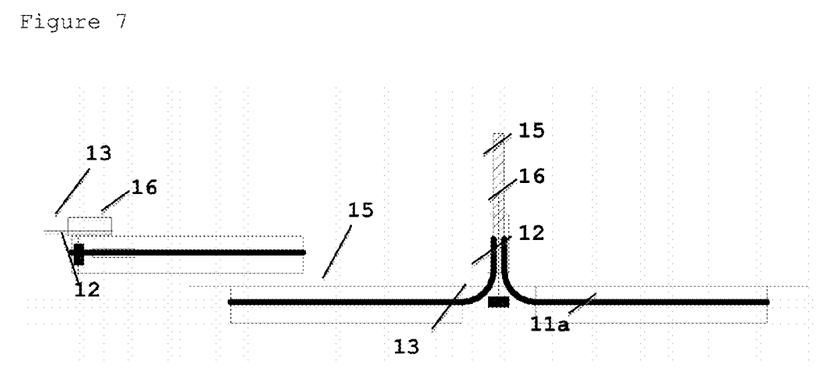

Since in the bed-monitoring devices as described herein the optical fiber is not fixed to the substrate support material it may inadvertently be removed. It can slide out of the guiding means and the support members surrounding it. Consequently, in a particular embodiment the bed-monitoring device is further characterized in that it comprises at least one anchoring mean (12,13) to hold and prevent the optical fiber from sliding out of the bed-monitoring device. In a particular embodiment said anchoring means is/are present at the entrance and/or exit of the optical fiber with the overlocked bag. It is an anchor in that it will prevent the optical fiber from being removed, but still gives it a certain space trough the presence of an anchor rode. As such, the anchor part (13) is fixed to the overlocked bag and the anchor rode (12) to the optical fiber, such as for example using a heat shrink (16).

Figure 6:
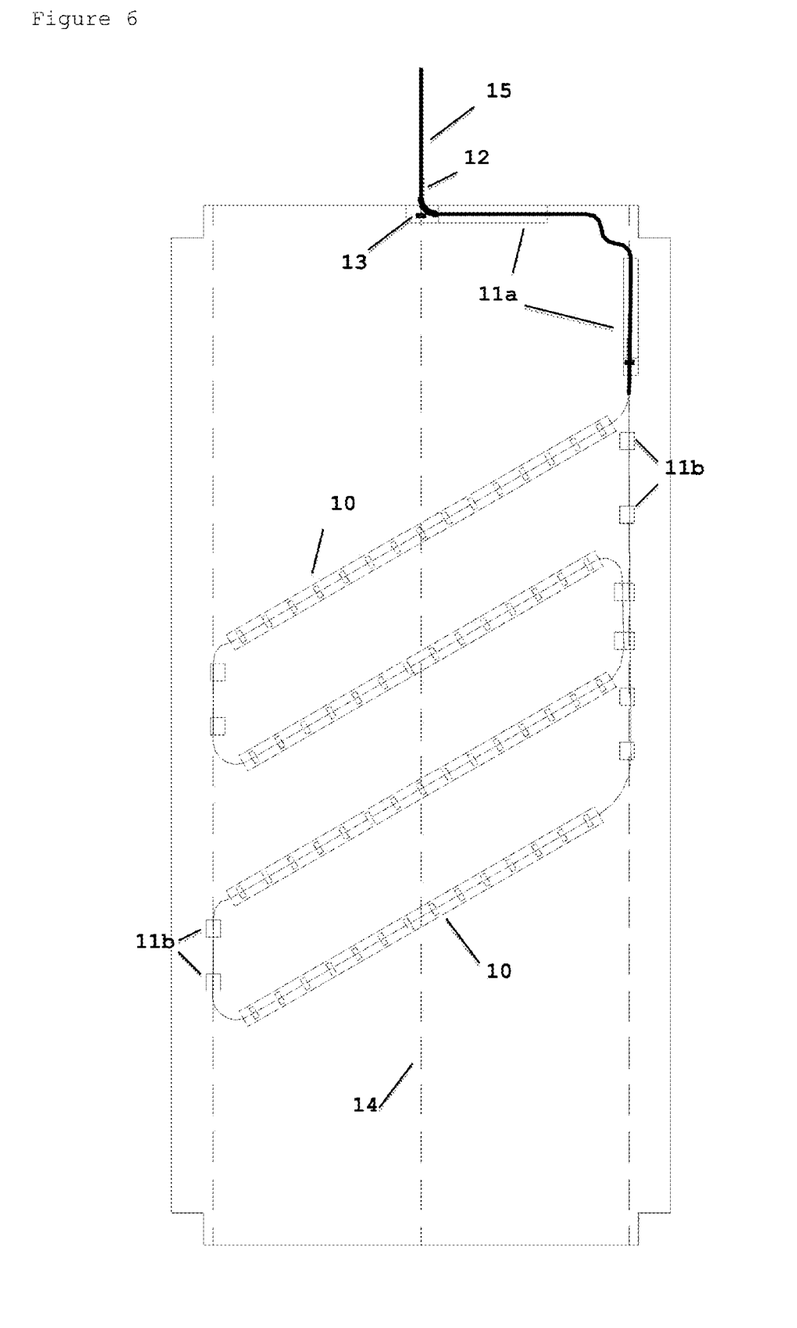
FIG. 6. Sewing design for the base of an overlock bag of the present invention having the measuring zones, consisting of the support members (10) comprising the pressure points (9), at the lower back, hip and upper leg region of the sleeping environment. Guiding members (11) are present in-between each of said measuring zones and at the top and side-member of said base. Anchoring means (details given in FIG. 7) at said top and side-member guiding means prevent in advert removal of the optical fiber. The centre of the base member is indicated with dotted line 14.

A further exemplary embodiment of the bed-monitoring device according to the present invention, and particularly useful in assessing presence and/or absence of a person, is provided in FIG. 6. In said instance the measuring zones, consisting of the support members (10) comprising the pressure points, are solely present at the lower back, hip and upper leg zone of the sleeping environment. Further guiding members (11) are present in-between each of said measuring zones and at the top and side-member of the substrate support material. Again, said guiding members include long sleeve like guiding means (11a) in the upper perimeter of the sleeping environment and one ore more short ring-like sleeves (11b) in-between the measuring zones.

As such it provides a mattress cover for detecting assessing presence and/or absence of a person; said mattress cover comprising a top panel and a bottom panel, wherein the top panel consists of an overlocked bag as described herein, and characterized in that the optical fibre is allocated at the lower back, hip and upper leg zone of the sleeping environment, more in particular with the measuring zones at the lower back, hip and upper leg zone of the sleeping environment.

The invention claimed is:

1. A bed-monitoring device comprising an optical fiber fixed within an overlocked bag consisting of a top layer and a base, wherein the optical fiber is interlocked at the base of said overlocked bag using one or more support members defining measuring zones along said optical fiber and characterized in that said support members surround said optical fiber and comprise pressure points at regular intervals; and wherein the optical fiber is not fixed to the support members in order to allow movement of the optical fiber for adaptability of the bed monitoring device to changes in shape and/or orientation of a sleeping environment.

2. The bed monitoring device according to claim 1, wherein the support members defining said measuring zones are made of a flexible, pliant material comprising pressure points at regular intervals, characterized in that the flexible, pliant material making up the support members accommodates changes in shape or orientation of a bed mattress without creating undesired kinks or breaks in the optical fiber.

3. The bed monitoring device according to claim 2, wherein the pressure points at said support members are made from hard, rigid materials, characterized in that the hard, rigid materials maintain a minimal spacer width when compressed by a user of the bed-monitoring device.

4. The bed monitoring device according to claim 1, wherein said support members consist of bands, slabs or strips made of a woven or non-woven fabric.

5. The bed monitoring device according to claim 2, wherein the pressure points alongside the length of the support members are spaced from one another at about every 1 cm to about every 10 cm.

6. The bed monitoring device according to claim 1, wherein the support members surrounding the optical fiber and defining the measuring zones, form a sleeve or tube that slidably fits around the optical fiber.

7. The bed-monitoring device according to claim 1, wherein the top layer consists of a fabric with a high weight.

8. The bed-monitoring device according to claim 7, wherein the fabric of the top layer has a weight of at least 150 g/m$^2$.

9. The bed-monitoring device according to claim 1, wherein the base consists of a fabric with a low weight.

10. The bed-monitoring device according to claim 9, wherein the fabric with a low weight is a knitted fabric having a weight of up to about 200 g/m$^2$.

11. The bed-monitoring device according to claim 1, wherein the top layer of the overlocked bag consists of a spacer knitwear or spacer fabric comprising standard filler materials.

12. The bed-monitoring device according to claim 1, wherein the base of the overlocked bag consists of an elastic fabric.

13. The bed-monitoring device according to claim 1, wherein both of the top layer and the base comprise knitted fabrics or woven fabrics.

14. The bed-monitoring device according to claim 1, wherein the base and the top layer of the overlocked bag are removably attached to one another.

15. The bed-monitoring device according to claim 1, wherein
the bed-monitoring device is part of a mattress cover.

16. The mattress cover as defined in claim 15, wherein the overlocked bag comprising the optical fiber constitutes at least one of a top panel or a bottom panel of said mattress cover.

17. The mattress cover according to claim 16, wherein the top panel is removably attached to the bottom panel of said mattress cover.

18. The mattress cover according to claim 16, wherein the at least one of the top panel or the bottom panel comprising the optical fiber is composed of a multi-layered fabric comprising a high weight filler of at least 150 g/m$^2$ as the top layer and a low weight back layer as the base.

19. The mattress cover according to claim 16, wherein the top panel comprising the optical fiber is composed of a multi-layered fabric comprising a high weight filler of at least 150 g/m$^2$ as the top layer and a low weight back layer as the base; and wherein the bottom panel is composed of a multi-layered fabric comprising a high weight filler of at least 150 g/m$^2$.

20. The mattress cover according to claim 16, wherein the bottom panel comprising the optical fiber is composed of a multi-layered fabric comprising a high weight filler of at least 150 g/m$^2$ as the top layer and a low weight back layer as the base; and wherein the top panel is composed of a multi-layered fabric comprising a high weight filler of at least 150 g/m$^2$.

21. The mattress cover according to claim 16, wherein the optical fiber in the top panel is located in the circumference of the mattress top panel.

22. The mattress cover according to claim 20, wherein the measuring zones of the optical fiber in the top panel are situated in the lower back, hip, and upper leg zone.

23. The mattress cover according to claim 20, wherein the optical fiber in the bottom panel is arranged in a plurality of stripes of wavy lines across the width of the mattress cover.

24. The mattress cover according to claim 23, wherein the measuring zones of the optical fiber in the bottom panel are situated in the lower back, hip and upper leg zone.

25. The mattress cover according to claim 24, wherein the optical fiber is arranged in at least 3 stripes of wavy lines across the width of the mattress cover.

* * * * *